(12) United States Patent
Brown (10) Patent No.: US 11,246,600 B1
(45) Date of Patent: Feb. 15, 2022

(54) SURGICAL LIGATION CLIP WITH ADVANCED INCISING MEANS AND BIFURCATED GUIDE TRACK

(71) Applicant: Geoff Brown, Cottonwood Height, UT (US)

(72) Inventor: Geoff Brown, Cottonwood Height, UT (US)

( * ) Notice: Subject to any disclaimer, the term of this patent is extended or adjusted under 35 U.S.C. 154(b) by 0 days.

(21) Appl. No.: 16/993,208

(22) Filed: Aug. 13, 2020

(51) Int. Cl.
*A61B 17/122* (2006.01)
*A61B 90/00* (2016.01)
*A61B 17/00* (2006.01)

(52) U.S. Cl.
CPC .. *A61B 17/122* (2013.01); *A61B 2017/00004* (2013.01); *A61B 2090/3966* (2016.02)

(58) Field of Classification Search
CPC . A61B 17/122; A61B 17/1227; A61B 17/083; A61B 17/1285; A61B 17/0487; A61B 17/282; A61B 17/08; A61B 17/12; A61B 2017/00004; A61B 2017/12004; A61B 2017/2926; A61B 2017/00584; A61B 2090/3966; B65D 33/1675

USPC ........................................................ 606/158
See application file for complete search history.

(56) References Cited

U.S. PATENT DOCUMENTS

| | | | |
|---|---|---|---|
| 6,863,675 B2 * | 3/2005 | Wilson, Jr. ........... | A61B 17/122 |
| 10,258,345 B2 * | 4/2019 | Brown ................. | A61B 17/122 |
| 2004/0193185 A1 * | 9/2004 | McBrayer ........... | A61B 17/1285 |
| | | | 606/142 |
| 2017/0209151 A1 * | 7/2017 | Brown ................. | A61B 17/122 |
| 2018/0168659 A1 * | 6/2018 | Bagaoisan ........... | A61B 17/122 |
| 2018/0368852 A1 * | 12/2018 | Foshee ................ | A61B 17/0487 |
| 2020/0360021 A1 * | 11/2020 | Foshee ................ | A61B 17/1227 |
| 2021/0030420 A1 * | 2/2021 | Pilletere ............... | A61B 17/122 |

\* cited by examiner

*Primary Examiner* — Melanie R Tyson
*Assistant Examiner* — Paige A Codrington
(74) *Attorney, Agent, or Firm* — Steven Rinehart (57) ABSTRACT

An advanced polymeric, surgical clip is provided for clamping a blood vessel between two legs. A hook section of the clip comprises two sharpened forward edges for penetrating connective tissue adjacent a vessel before closing the surgical about a blood vessel. The upper leg of the surgical clip may comprise an oblique flank for disposing over the one or more edge of the hook section, the lower surface of the oblique flank defining a channel in which a tip of the hook section travels.

11 Claims, 8 Drawing Sheets

SURGICAL LIGATION CLIP WITH ADVANCED INCISING MEANS AND BIFURCATED GUIDE TRACK

FIELD OF THE INVENTION

This invention relates to surgical clips used to stop blood flow through blood vessels during surgery, and more particularly relates to a ligation clip for piercing connective tissue and locking down on a blood vessel.

BACKGROUND

Description of the Related Art

During surgery, blood vessels, including veins or arteries, must be ligated to stop blood flow to a surgical site. In some cases, physicians must cut these vessels, or in other cases restrict them. Ligation is realized using one or more ligation clips which are relatively easy and quick to apply. Accordingly, the use of ligating clips in endoscopic as well as open surgical procedures has grown dramatically.

The ligation clips are applied to the blood vessel using a hemostatic ligation clip applier. Blood vessels remain ligated after surgery until occlusion occurs. Although in the past, surgical or ligation clips have been fabricated from metal, most current ligation clips are polymeric to prevent interference from the clip with imaging devices, including x-ray and MRI machines.

Typical ligation clips in the art are blunt and/or do not pierce soft connective tissue surrounding a blood vessel in surgically efficient manner. It also cumbersome to remove ligation clips from blood vessels, sometimes resulting in ligation clips being mistakenly left in the soft tissue or patients, or collateral soft tissue being damaged with removal.

A clip applier specifically designed for asymmetric plastic clips is used to close the clip around the tissue to be ligated, and to latch or lock the clip in the closed condition. When compressed the clip applier forces the legs of traditional clips inward and locks them together around a blood vessel.

Although polymeric ligation clips are in the art, current clips suffer from several inefficiencies, including that current clips do not efficiently pierce soft tissue and leave sharpened edges exposed to cut, damage and irritate tissue during surgery. There exists a need in the art for a surgical ligation clip which more precisely cuts tissue during surgery. A device which overcomes these inefficiencies is desirable.

SUMMARY

From the foregoing discussion, it should be apparent that a need exists for an improved surgical ligation clip. Beneficially, such a device would overcome inefficiencies with the prior art by providing a clip which could more efficiently penetrate soft tissue and prevent soft tissue damage.

The present invention has been developed in response to the present state of the art, and in particular, in response to the problems and needs in the art that have not yet been fully solved by currently available systems and apparati. Accordingly, the present invention has been developed to provide a polymeric surgical ligation clip, the surgical clip comprising: an elongated concave lower leg having a rearward end and a forward end; an elongated upper leg having a rearward end hingedly connected to the rearward end of the lower leg, the elongated upper leg comprising at a forward tip a bifurcated guide track comprising: two prongs diverging from the upper leg, the prongs defining a recess between them adapted to receive and guide the hook section as it travels upwardly; a plurality of teeth protruding outwardly from one or more of the lower leg and the upper leg; a hook section jutting outwardly from the lower leg and cantilevers over the lower leg, the hook section defining and lower leg together defining a latching recess for engaging a distal end of the upper leg, the hook section having a forward edge and a rearward edge, the rearward edge sharpened for incising soft tissue when the surgical ligation clip is closed within soft tissue; wherein the hook section further comprises two sharpened forward edges on a forward the surface of the hook section, a recess forming between the two forward edges; an oblique flank connected to the distal end of the upper leg, the oblique flank extending from the upper leg at a location proximal to a terminal distal end of the upper leg; wherein the oblique flank protrudes outwardly from the upper leg to a point more than the terminal distal end of the upper leg; wherein a recess is created between a lower surface of the oblique flank and an upper surface of the upper leg; the oblique flank adapted to prevent damage to soft tissue during surgery and postoperatively, a lower edge of the oblique flank defining a channel in which the tip of the hook section travels rearwardly as it penetrates soft tissue.

The plurality of teeth may be chevron-shaped. The oblique flank may be formed as an integrated piece with the upper leg.

The entire surgical clip may be formed as one integrated piece.

The distal end of the upper leg may further comprise a distal tooth for piercing soft tissue. The surgical clip may further comprise a plurality of bosses for engaging jaws of an applier.

A stress cavity is formed at the connection point of the upper leg and the lower leg. The hook may further comprise a sharpened forward edge. The hook section may further comprise a sharpened tip in some embodiments. The surgical clip is fabricated from one or more bioabsorbable materials.

The surgical clip may be rendered radio opaque in still further embodiments.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. The order in which a particular method occurs may or may not strictly adhere to the order of the corresponding steps shown.

Figure 1:
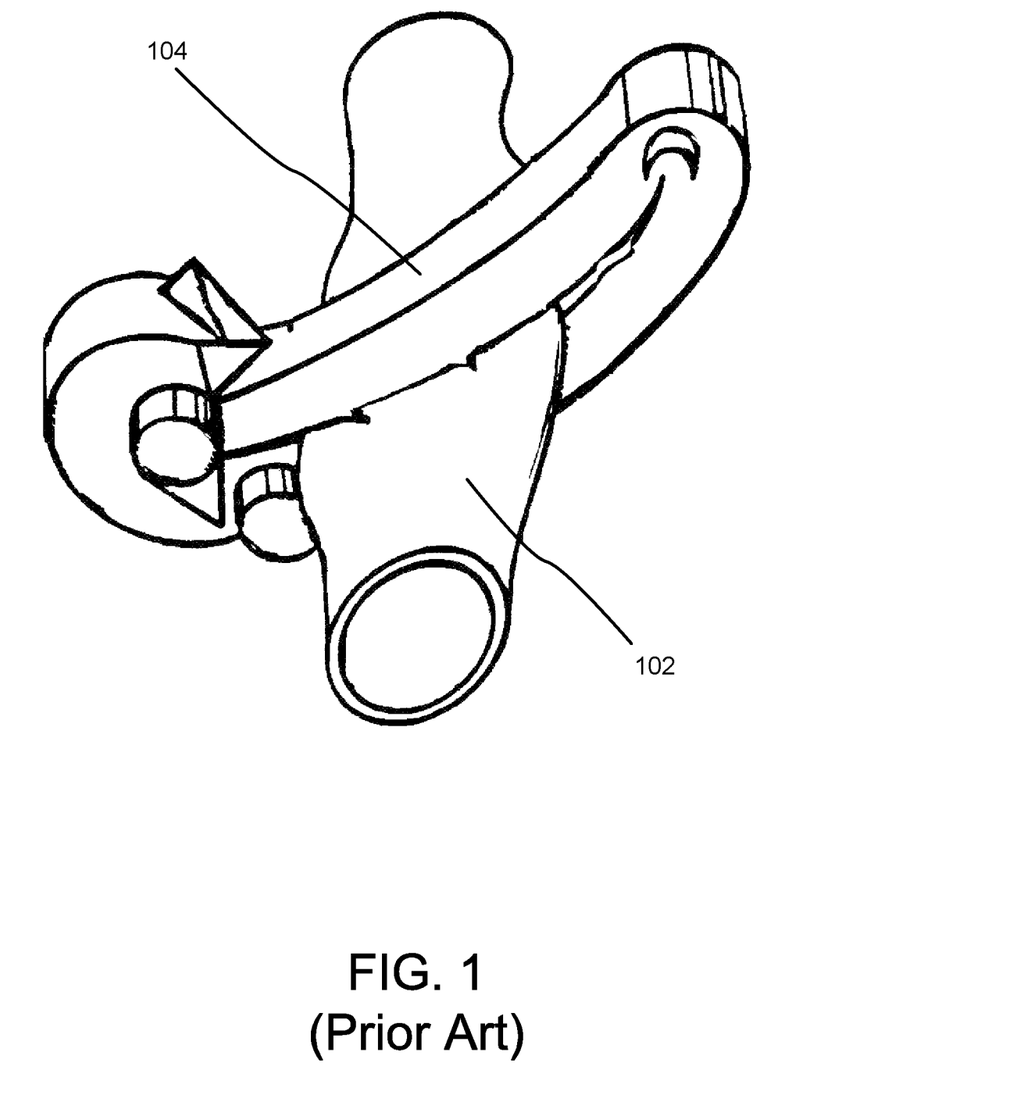
FIG. 1 is a traditional ligation clip in accordance with the prior art.

FIG. 1 is a traditional ligation clip in accordance with the prior art.

As shown, the conventional surgical clip 104 clamps down on a blood vessel 102. The surgical clip 104 is inserted using a specialized clamping or crimping tool (i.e. forceps). A hook portion of the surgical clip 104 clamps down on the blood vessel 102 and ligates the blood vessel 102.

The surgical clip 104 may be made of biodegradable materials and comprises latching means to keep the surgical clip 104 closed. Typically the surgical clip 104 is left in place permanently.

Figure 2:
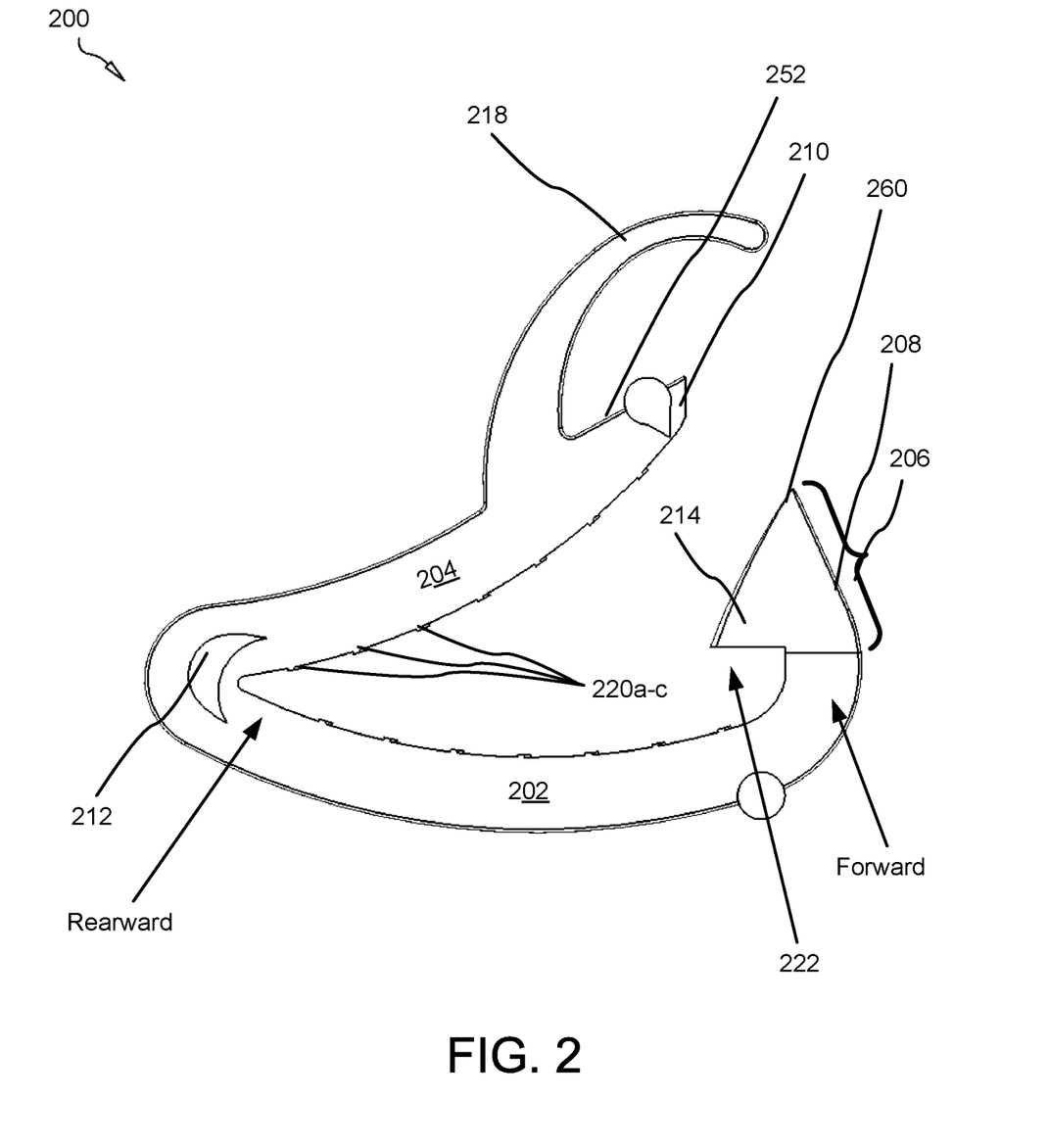
FIG. 2 is a side perspective view of a surgical ligation clip with advanced incising means in accordance with the present invention.

FIG. 2 is a side perspective view of a surgical ligation clip with advanced incising means 200 in accordance with the present invention. The surgical clip 200 comprises a lower leg 202; an upper leg 204; hook section 206 having a sharpened forward edge 208, a sharpened tip 260 and a hook 214; an oblique flank 218; a distal tooth 210; and a stress recess 212.

The surgical clip 200 may be fabricated from polymeric, metallic, and/or biodegradable materials. The use of polymeric and/or biodegradable materials to form the surgical clip 200 may beneficially render the surgical clip radio opaque for imaging purposes.

The lower leg 202 and upper leg 204 comprises elongated convex members hingedly connected at their rearward ends. The connection point between the legs 202, 204 defines a stress recess 212 for relieving tensile forces exerted across the hinge or connection point between the legs 202, 204 by a closing or closed clip 200 in the latched position (the clip 200 is shown in the open position).

The tip 260 of the hook section 206 may be sharpened to pierce soft tissue when the clip 200 in closed within a patent during surgery. For this reason, the tip 260 of the hook section 206 of the clip 200 protrudes upwardly away from the lower leg in tooth-like fashion.

The inner surface of the leg 204 is contoured to match the outer (i.e., upper) surface of the leg 202 (both have approximately the same radius curvature) for extending compressive or tensile force uniformly across the legs 202, 204.

The clip 200 comprises a peninsular hook section 206, which protrudes, in the shown embodiment, in triangular fashion, from the lower leg 202 and which cantilevers back over the inner surface of the lower leg 202 forming a latching recess 222. The hook section 206 latches over the distal end 210 (or distal tooth) of the upper leg 204 when the clip 200 is compressed into closed.

In the closed position, the oblique flank 218 may be configured to clamp down over the sharpened forward edge 208 of the hook section 206 (or additionally or alternatively a corresponding sharpened rearward edge further described below), covering the sharpened forward edge 208 and preventing the edge 208 from incising, piercing, or agitating soft tissue in position operatively or post-operatively.

Notably, the upper edge 252 of the upper leg 204 which is disposed (or positions) beneath the oblique flank 218 is sharpened, and adapted to incise tissue caught between the hook section 206 and the upper edge 252. The upper edge of the upper leg 204 which does not position beneath the oblique flank 218 is typically not sharpened in the preferred embodiment.

Figure 3:
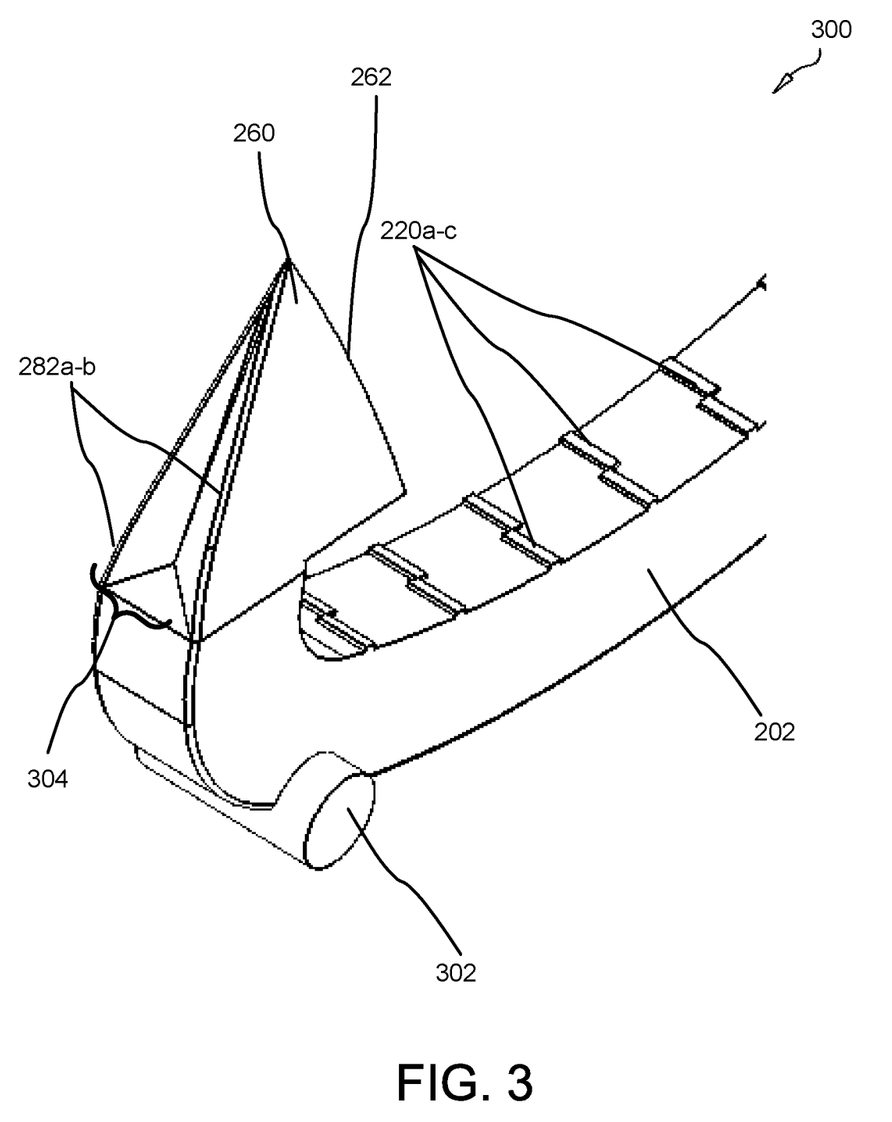
FIG. 3 is an upper-elevational, forward, side perspective view of the hook section of a surgical ligation clip with advanced incising means in accordance with the present invention.

FIG. 3 is an upper-elevational, forward, side perspective view of the hook section of a surgical ligation clip with advanced incising means 300 in accordance with the present invention. As shown, the inner edge of the lower leg 202 comprises a plurality of staggered teeth 220. The teeth 220 in the shown embodiment are staggered along opposing sides of the inner edge of the lower leg 202. In some embodiments, the teeth 220 are not staggered on alternating sides of the inner edge of the lower leg 202, but rather span the entire width of the inner edge of the lower leg 202 at regular or irregularly-spaced intervals.

Notably, the forward perimeter of the hook section 206 comprises two sharpened edges 282 to facilitate incising or piercing of soft tissue as the clip 200 in inserted into an anesthetized patient during surgery. The surface between these two sharpened edges 282 is concave, or otherwise recessed inward, to define a recess 304 between the sharpened edges 282. The two sharpened edges 282 converge at the sharpened tip 260. The two sharpened edges 282 become progressively more blunt as they diverge away from each other and join the lower leg 202.

Figure 4:
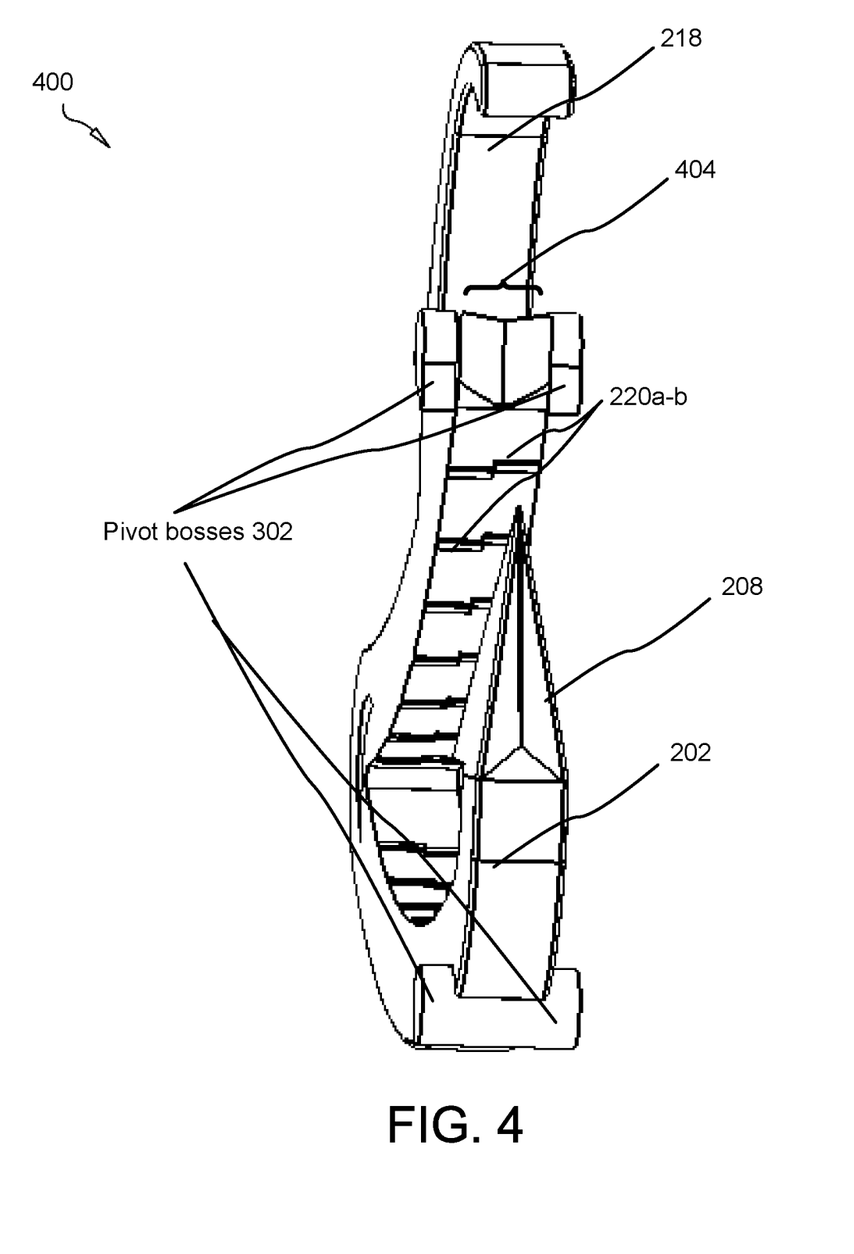
FIG. 4 is a forward perspective view of a surgical ligation clip with advanced incising means in accordance with the present invention.

FIG. 4 is a forward perspective view of a surgical ligation clip with advanced incising means 400 in accordance with the present invention. The clip 400 comprises a plurality of bosses 302.

The bosses 302 are cylindrical in the shown embodiments, and protrude laterally from the body lower leg 202. The bosses 302 allow an applicator, or clamping tool (i.e. forceps) to engage the clip 400 and insert the clip 400 in open or semi-open position into soft tissue during the operative phase of surgery by a surgeon, as known to those of skill in the art.

The distal tooth 210 of the upper leg 204 comprises a bifurcated guide track 404. The forward tip of the distal tooth 210 separates into two prongs 502*a-b* (further described below) which are adapted to form a guide track in which the hook section 206 is guided upwardly.

Figure 5:
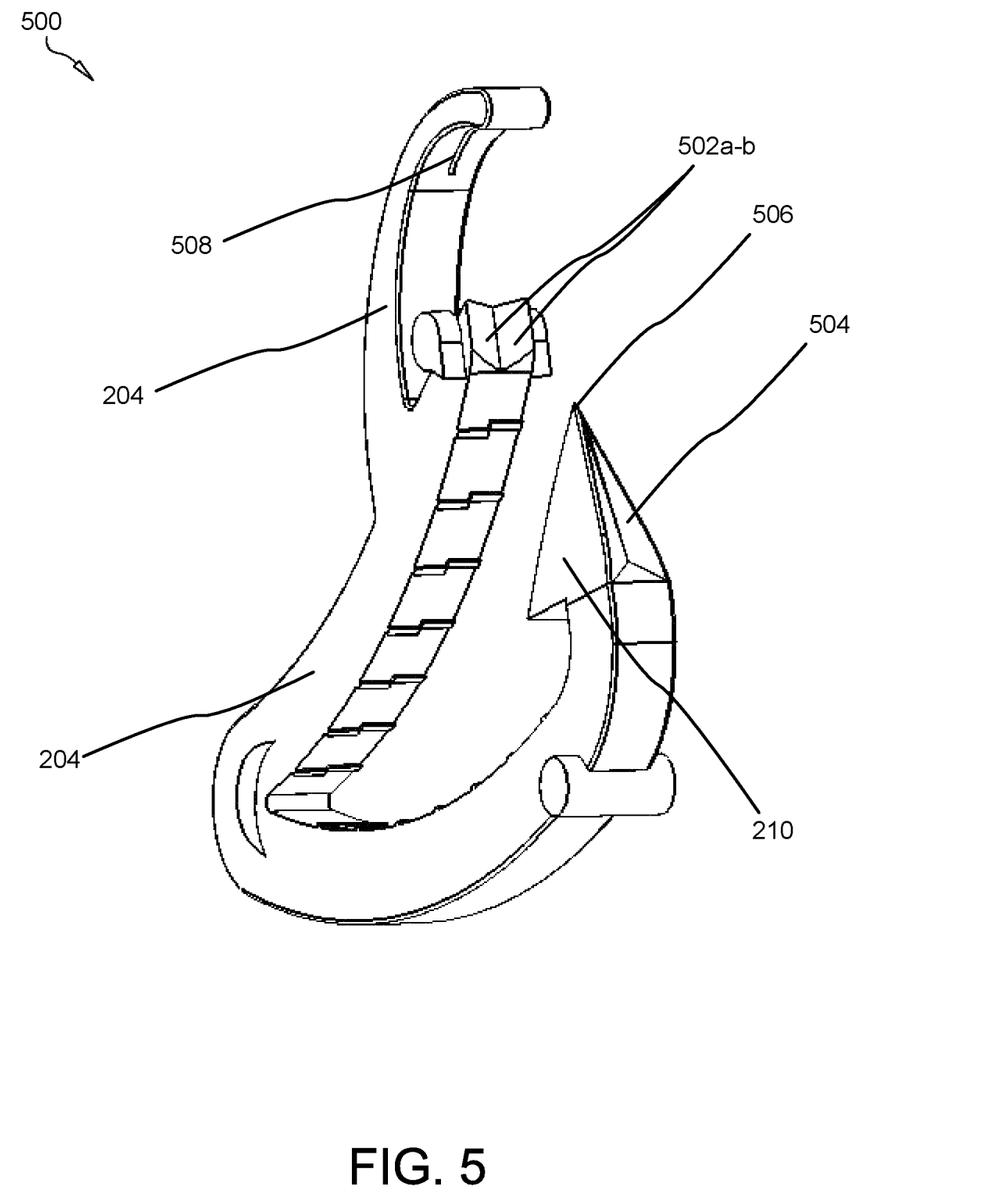
FIG. 5 is a lower, forward perspective view of a surgical ligation clip with advanced incising means in accordance with the present invention.
Figure 6:
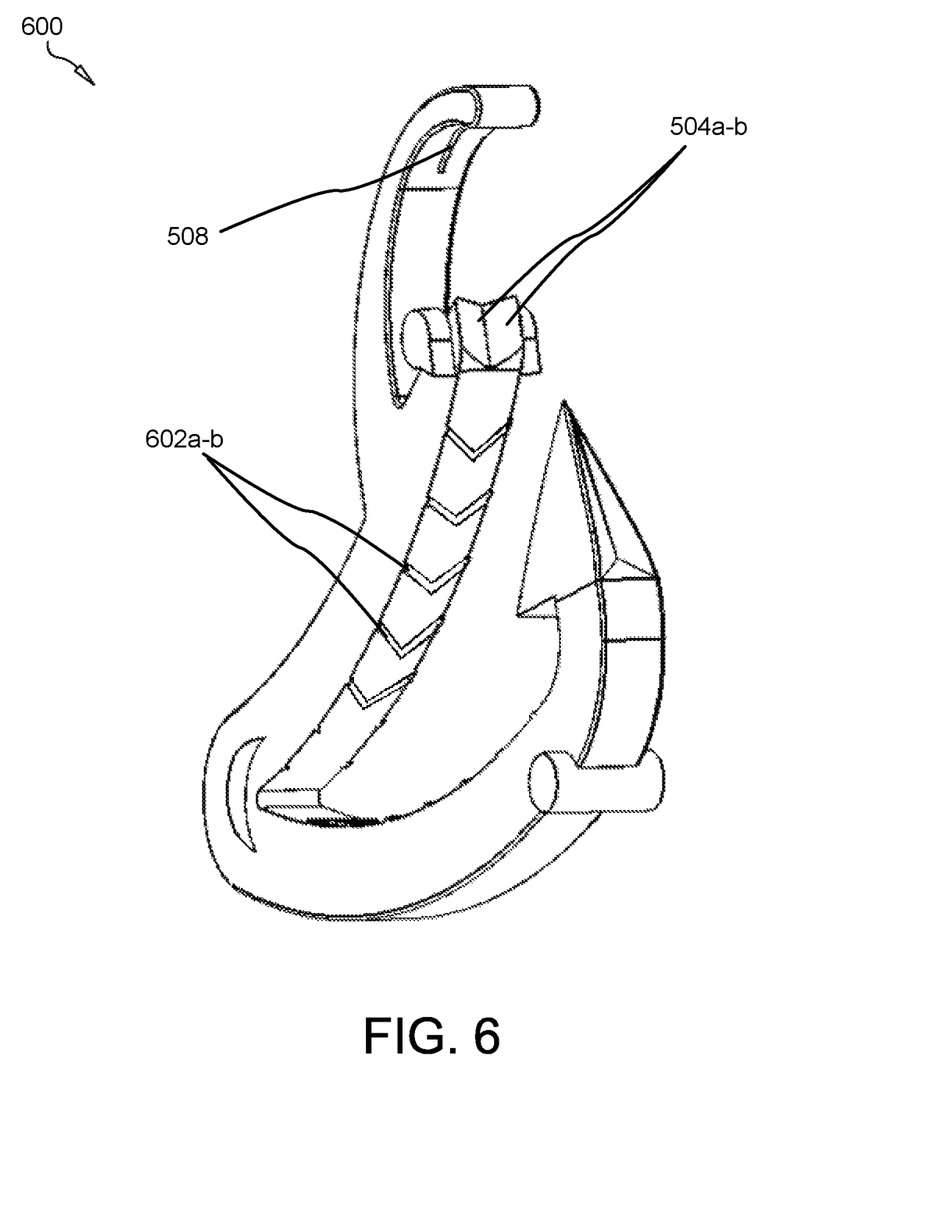
FIG. 6 is a lower, forward perspective view of a surgical ligation clip with advanced incising means in accordance with the present invention.

FIG. 5-6 illustrate a top perspective view of an improved surgical ligation clip 500, 600 in accordance with the present invention.

The rearward edge of the hook section 206 positions between the prongs 502*a-b* and the bifurcated guide track 404 guides the hook section 206 into position as it is forced upwardly as the clip is closed. The prongs 502*a-b* provide lateral support to the hook section as it is forced upwardly and guide the tip 260 of the hook section into the channel 508.

The lower surface of the oblique flank 218 defines a channel 508 (or a track, guide track, or recess). The channel 508 receives the tip 260 of the hook section 206 and guides the tip 260 as the hook 214 travels rearwardly after the hook section 206 rises upwardly enough to clear the bifurcated guide track 404.

As the hook section 206 rises upwardly, as the bosses 302 are forced together, the tip 260 enters the channel 508, incising soft tissue as it goes. The bifurcated guide track 404 forces the hook section 206 forward as the hook section 206 rises. Once the hook section 206 clears the bifurcated guide track 404, the hook section 206 snaps rearwardly, being formed from polymeric materials which inherently bias the hook section 206 in that direction.

The teeth 602 shown in embodiment 600 are disposed on the upper edge of the lower leg 202 and lower edge of the upper leg 204 in embodiment 500. The teeth 602 may be chevron-shaped (or V-shaped) as shown, which provides more gripping function and less incising function as is desirable to grip (but not incise) blood vessels.

Figure 7:
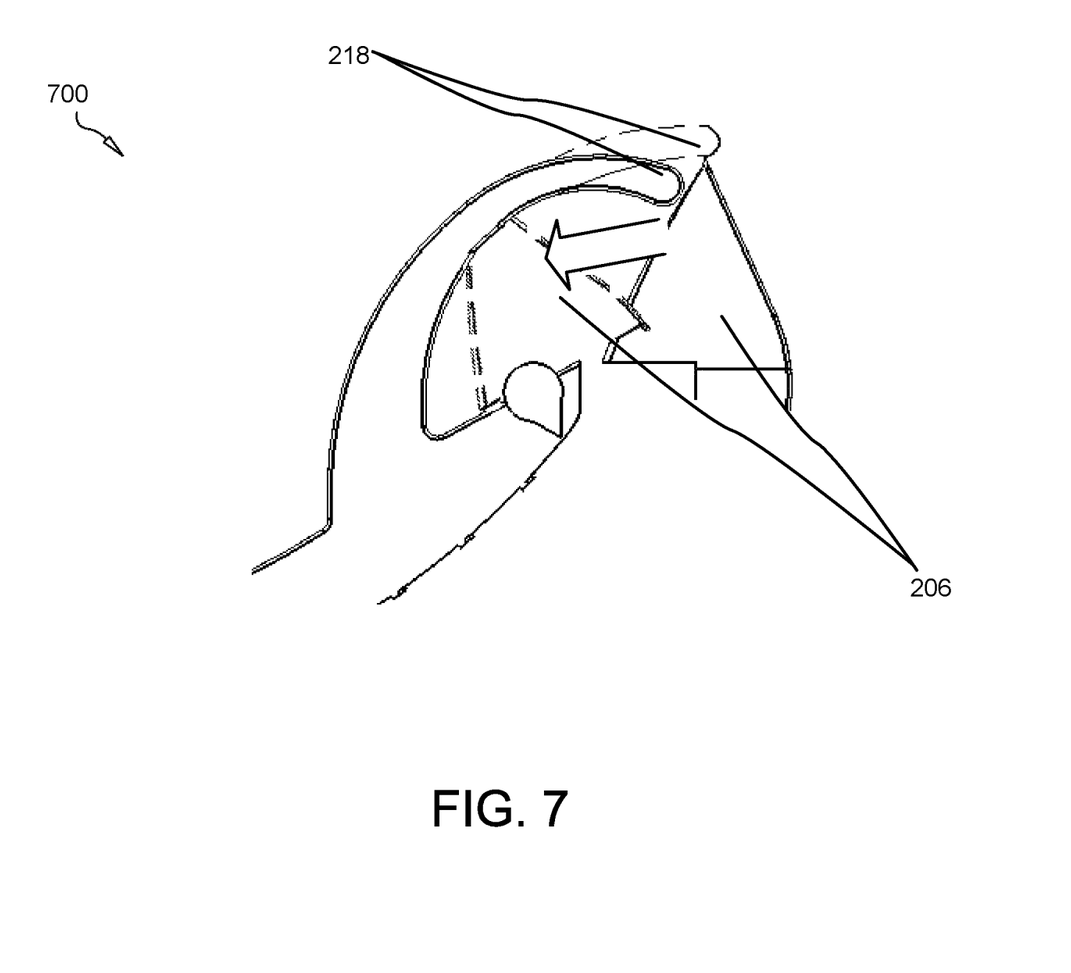
FIG. 7 is a lower, forward perspective view of a surgical ligation clip with advanced incising means in accordance with the present invention.

FIG. 7 is a lower, forward perspective view of a surgical ligation clip with advanced incising means in accordance with the present invention.

The natural formation of the polymeric hook section 206 biases the hook section 206 toward the rear of the oblique flank 218, with the tip 260 received in the channel 508. As the hook section 206 clears the bifurcated guide track 218, the hook section 206 travels rearwardly within the channel 508.

Figure 8:
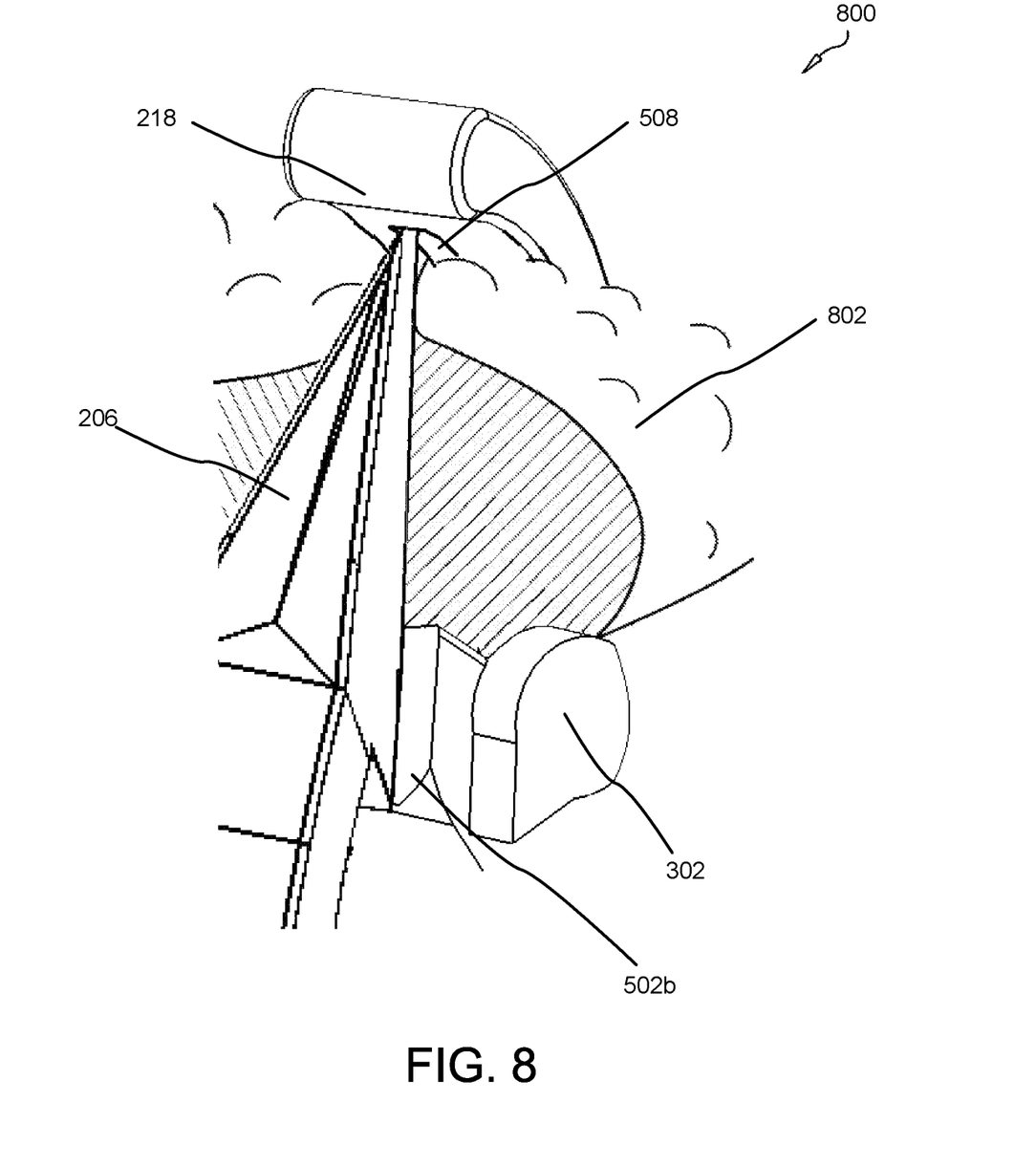
FIG. 8 is an environmental perspective view of a surgical ligation clip with advanced incising means in accordance with the present invention.

FIG. 8 is an environmental perspective view of a surgical ligation clip with advanced incising means 800 in accordance with the present invention.

The oblique flank 218 and hook section 206 are shown with soft tissue 802 between them being incised by the forward edge 262 of the hook section 206 as the hook section 206 travels within the groove 508. The tissue 802 is incised by the snapping, forward motion of the leading edge 262 of the hook section.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A polymeric surgical ligation clip, the surgical clip comprising:
    an elongated concave lower leg having a rearward end and a forward end;
    an elongated upper leg having a rearward end hingedly connected to the rearward end of the lower leg, the elongated upper leg comprising at a forward tip a bifurcated guide track comprising:
        two prongs diverging from the upper leg, the prongs defining a recess between them adapted to receive and guide a hook section as it travels upwardly;
    a plurality of teeth protruding outwardly from one or more of the lower leg and the upper leg;
    a hook section jutting outwardly from the lower leg and cantilevers over the lower leg, the hook section and lower leg together defining a latching recess for engaging a distal end of the upper leg, the hook section having a forward edge and a rearward edge, the rearward edge sharpened for incising soft tissue when the surgical ligation clip is closed within soft tissue;
    wherein the hook section further comprises two sharpened forward edges on a forward surface of the hook section, a recess forming between the two forward edges; and
    an oblique flank connected to the distal end of the upper leg, the oblique flank extending from the upper leg at a location proximal to a terminal distal end of the upper leg; wherein the oblique flank protrudes outwardly from the upper leg to a point more than the terminal distal end of the upper leg; wherein a recess is created between a lower surface of the oblique flank and an upper surface of the upper leg; the oblique flank adapted to prevent damage to soft tissue during surgery and postoperatively, a lower edge of the oblique flank defining a channel in which the tip of the hook section travels rearwardly.

2. The surgical clip of claim 1, wherein the plurality of teeth are chevron-shaped.

3. The surgical clip of claim 1, wherein the oblique flank is formed as an integrated piece with the upper leg.

4. The surgical clip of claim 1, wherein the entire surgical clip is formed as one integrated piece.

5. The surgical clip of claim 1, wherein the distal end of the upper leg further comprises a distal tooth for piercing soft tissue.

6. The surgical clip of claim 1, further comprising a plurality of bosses for engaging jaws of an applier.

7. The surgical clip of claim 1, where a stress cavity is formed at the connection point of the upper leg and the lower leg.

8. The surgical clip of claim 1, wherein the hook section further comprises a sharpened forward edge.

9. The surgical clip of claim 1, wherein the hook section further comprises a sharpened tip.

10. The surgical clip of claim 1, wherein the surgical clip is fabricated from one or more bioabsorbable materials.

11. The surgical clip of claim 1, wherein the surgical clip is rendered radio opaque.

* * * * *